United States Patent
Ludtke et al.

(10) Patent No.: US 11,352,596 B2
(45) Date of Patent: Jun. 7, 2022

(54) METHOD AND PLANT FOR PRODUCING BIOGAS FROM LIGNOCELLULOSE-CONTAINING BIOMASS

(71) Applicant: Verbio Vereinigte Bioenergie AG, Leipzig (DE)

(72) Inventors: Oliver Ludtke, Markkleeberg (DE); Michael Schlimbach, Halle (DE); Enrico Fichter, Leipzig (DE); Jens Horn, Leipzig (DE); Georg Pollert, Berlin (DE); Jan Kuhling, Halle (DE)

(73) Assignee: VERBIO VEREINIGTE BIOENERGIE AG, Leipzig (DE)

( * ) Notice: Subject to any disclaimer, the term of this patent is extended or adjusted under 35 U.S.C. 154(b) by 0 days.

(21) Appl. No.: 14/654,632

(22) PCT Filed: Dec. 16, 2013

(86) PCT No.: PCT/EP2013/076630
§ 371 (c)(1),
(2) Date: Jun. 22, 2015

(87) PCT Pub. No.: WO2014/095669
PCT Pub. Date: Jun. 26, 2014

(65) Prior Publication Data
US 2016/0230134 A1   Aug. 11, 2016

(30) Foreign Application Priority Data

Dec. 21, 2012   (DE) ..................... 10 2012 112 898.7

(51) Int. Cl.
C12P 5/02 (2006.01)
C12M 1/107 (2006.01)
(Continued)

(52) U.S. Cl.
CPC ............ *C12M 21/04* (2013.01); *C12M 27/02* (2013.01); *C12M 29/02* (2013.01); *C12M 45/04* (2013.01);
(Continued)

(58) Field of Classification Search
CPC ...... C12M 21/04; C12M 27/02; C12M 45/04; C12M 45/20; C12M 45/02;
(Continued)

(56) References Cited

U.S. PATENT DOCUMENTS

2010/0108567 A1* 5/2010 Medoff .................... C10G 3/00
208/49
2011/0020884 A1* 1/2011 Latouf ...................... C12P 7/10
435/136
(Continued)

FOREIGN PATENT DOCUMENTS

CN   101358218 A   *  2/2009
DE   2543939 A1      7/1977
(Continued)

OTHER PUBLICATIONS

Zhang et al., Biores. Technol., 1999, 68: 235-245. (Year: 1999).*
(Continued)

*Primary Examiner* — Allison M Fox
*Assistant Examiner* — Qing Xu
(74) *Attorney, Agent, or Firm* — Westman, Champlin & Koehler, P.A.

(57) ABSTRACT

The invention relates to a method for producing biogas from lignocellulose-containing biomass, preferably from straw, and to a plant for carrying out said method.

6 Claims, 2 Drawing Sheets

(51) Int. Cl.
*C12M 1/00* (2006.01)
*C12M 1/06* (2006.01)
*C12P 19/14* (2006.01)

(52) U.S. Cl.
CPC .............. *C12M 45/20* (2013.01); *C12P 5/023* (2013.01); *C12Y 304/00* (2013.01); *C12Y 404/01026* (2015.07); *C12P 19/14* (2013.01); *C12P 2201/00* (2013.01); *C12P 2203/00* (2013.01); *Y02E 50/30* (2013.01); *Y02P 20/582* (2015.11)

(58) Field of Classification Search
CPC ........... C12Y 404/01026; C12Y 304/00; C12P 5/023; C12P 2201/00; C12P 2203/00; C12P 5/00; C12P 5/02; Y02E 50/30; Y02P 20/582
See application file for complete search history.

(56) References Cited

U.S. PATENT DOCUMENTS

| | | | | |
|---|---|---|---|---|
| 2013/0230624 | A1* | 9/2013 | Augustin | C12N 13/00 426/53 |
| 2013/0252293 | A1* | 9/2013 | Chen | C07D 307/48 435/139 |

FOREIGN PATENT DOCUMENTS

| | | | |
|---|---|---|---|
| DE | 79 01 636 | U1 | 6/1979 |
| DE | 4414459 | A1 | 11/1995 |
| DE | 102008024388 | A1 | 4/2009 |
| DE | 10 2008 004 971 | A1 | 7/2009 |
| EP | 0377832 | A2 | 7/1990 |
| EP | 1978086 | A * | 10/2008 |
| EP | 1978086 | A1 | 10/2008 |
| WO | 01/60752 | A1 | 8/2001 |
| WO | 2006/042551 | A1 | 4/2006 |
| WO | 2009/000305 | A1 | 12/2008 |
| WO | WO 2009/000305 | A * | 12/2008 |
| WO | 2009/016082 | A2 | 2/2009 |

OTHER PUBLICATIONS

Li et al., Int. J. Hydrogen Energy, 2010, 35: 7261-7266. (Year: 2010).*
International Search Report and Written Opinion for PCT Application No. PCT/EP2013/076630, dated Sep. 5, 2014, 22 pages.
Bauer, Alexander et al., "Analysis of methane potentials of steam-exploded wheat straw and estimation of energy yields of combined ethanol and methane production", Journal of Biotechnology 142 (2009) 50-55, Elsevier B.V., 2009, 3 pages.
English translation of International Preliminary Reporton Patentability for PCT Application No. PCT/EP2013/076630, dated Jun. 23, 2015, 14 pages.
German Search Report for German Patent Application No. 10 2012 112 898.7, dated Jul. 9, 2013, 5 pages.
Presentation, Ventury GmbH, "Thermische Druckwechselkonditionlerung", Chemnitz GutureGas, Biomateg, dated Dec. 5, 2012, 24 pages.
Third Party Observations from European Patent Application No. EP 13 807 989.2-1501, dated Apr. 11, 2017, 27 pages.
Opposition against the grant of European Patent patent EP 2 935 595 B1, dated Jan. 7, 2021, 30 pages.
Machine translation of Reinhold, Dr. G., Lecture material "Fermentation of Straw—Status and Perspectives", 2nd International Straw Conference, Mar. 29-30, 2012, in Berlin, 14 pages.
Machine translation of Schwarz, B. et al., Presentation material "Potentials and economic viability of straw as a substrate in Wet fermentation plants", Energy Planting Day, in Trossin, on Aug. 29, 2012, 28 pages.
Machine translation of Schwarz, B. et al., Lecture material "Disintegration processes—effort and benefit for the Biogas production", FNR/KTBL Congress, Sep. 15 and 16, 2009, 32 pages.
Office Action, for German Patent Application No. 10 2012 112 898.7, dated Jun. 9, 2021, 12 pages.

* cited by examiner

METHOD AND PLANT FOR PRODUCING BIOGAS FROM LIGNOCELLULOSE-CONTAINING BIOMASS

CROSS-REFERENCE TO RELATED APPLICATION

This Application is a Section 371 National Stage Application of International Application No. PCT/EP2013/076630, filed 16 Dec. 2013 and published as WO 2014/095669 A2 on 26 Jun. 2014, in German, the contents of which are hereby incorporated by reference in their entirety.

BACKGROUND OF THE INVENTION

1. Technical Field

The invention relates to an integrally combined method and a corresponding plant for energy and resource-saving production of biogas from lignocellulose-containing biomass.

The need for a reduction in emissions of greenhouse gases, such as carbon dioxide ($CO_2$) caused by humanity, in order to counteract the climate change currently taking place is scientifically and socially recognized. At the same time, owing to the growing world population, the demand for food, drinking water and energy or final energy sources and fuels is rising. Novel methods and production processes must be directed towards these current requirements. The present invention addresses this demand and provides a method and a corresponding plant for producing biogas from previously little utilized lignocellulose-containing, nutritionally unusable biomass. The method and a corresponding plant can provide biogas by minimizing energy and water consumption in a resource-saving manner and with very high greenhouse gas-minimization potential in comparison to fossil energy sources.

2. Description of the Prior Art

The production of biogas from lignocellulose-containing biomass in principle also takes place like the fermentation of liquid manure and sustainable raw materials (SRM) by means of the steps: processing of the lignocellulose-containing biomass, mixing with water, anaerobic fermentation by microorganisms via the intermediate steps hydrolysis, acidogenesis, acetogenesis and methanogenesis and as a rule processing of the fermentation wastes and the biogas generated.

Also, for a high biogas yield, lignocellulose-containing biomass such as for example straw is beneficially treated in such a manner that the lignin deposited in the cell walls is broken up and/or degraded and as a result the cellulose and hemicellulose contained are better accessible for the microbial anaerobic degradation. A range of generally known techniques exist for this which are, for example, based on the principles of mechanical shredding, thermal, chemical or enzymatic treatment and biological cleavage with fungi.

In addition, in-process water recycling is also known in the production of biogas from lignocellulose-containing biomass. Appropriate methods for recovery of process water are, for example, based on a simple phase separation by means of presses or decanter centrifuges.

In biogas technology, a known problem in the fermentation of fiber-containing raw materials, especially straw, is the formation of floating layers during the fermentation process. This is counteracted by thorough shredding of the fiber-containing material or by mechanical destruction of the floating layer.

It is further known that in the fermentation of mainly lignocellulose-containing material not all nutrients necessary for extensive microbiological conversion are present and have to be supplied into the fermentation process. However, as a rule it is not clear at what concentration the nutrients must be present. Recommendations from the literature are based on the fermentation of previously known substrates such as SRM and extend over a very wide concentration range of several powers of ten.

In WO2009016082A2 for example, a method for the conversion of biomass from sustainable raw materials is described, in which the fermentation residue from a first anaerobic fermenter is subjected to a solid-liquid phase separation, preferably by pressing, centrifugation or screening, and then the separated solids phase is processed by thermal pressure hydrolysis at at least 170° C. and a pressure of at least 1 MPa and a preferred duration from 10 mins to 120 mins, in order to feed it into an anaerobic fermenter again. In the process, ca 40% of the organic starting mass should be degraded and converted into biogas by the first fermentation process with an average duration of 25 days. In the second fermentation process, after the thermal pressure hydrolysis, with a duration of for example 20 days, it should be possible to increase the overall degradation level to 80%, a silage of non-agricultural wastes of 60% maize and 40% rye together with liquid manure being used as raw material.

The method described in WO2009016082A2 is explicitly based on sustainable raw materials, which are in general considered to include specifically cultivated biomass such as for example whole maize plants. There are a number of disadvantages, particularly in its application to biomass of high lignocellulose content such as for example straw. Thus the problem of floating layer formation in the fermentation is not considered. Further, the digestion process described is very energy and cost-intensive. Firstly, the processing of large quantities of fermentation wastes with screw presses for major concentration of the dry substance (DS) requires high energy consumption, and maintenance and investment expenditure. After the thermal pressure hydrolysis, the fermentation wastes enriched in the DS content must again be added to the previously separated liquid phase at least in part, in order to establish a DS content favorable for a fermentation. Thus the DS enrichment is provided exclusively for the in any case energy-intensive thermal pressure hydrolysis. In this, an approximately 30% solids phase must be conveyed, heated and cooled for a subsequent fermentation. Such a solids phase mainly consisting of fibers is, at least with the use of straw or straw fermentation wastes, no longer pumpable with conventional pumps. Furthermore, heat transfer of the very large quantities of energy into such a solids phase indirectly via a proposed flue gas heat exchanger from the flue gas of a CHP plant is associated with very high plant expenditure and correspondingly high costs.

Further, this design inevitably requires direct combustion of the generated biogas in the plant. Alternative heating by high-grade direct steam of at least 1.0 MPa would, for the charging operation described, be markedly degraded during the pressure release and, since no further utilization is indicated, would be lost. In addition, the method describes the mixed use of biomass and other starting substances necessary for the methanogenesis, such as for example liquid manure and/or sewage sludges and is not suitable for an anaerobic fermentation, exclusively of lignocellulose-containing biomass such as for example straw. This is also clear from the fact that the in-process recycling of a liquid phase necessary for efficient straw fermentation is not described.

The patent specification WO2009000305A1 describes a plant and a method for generation of biogas in a fermenter by anaerobic bacterial fermentation of biomass, especially straw, with a chemical, mechanical and/or thermal digestion being performed and the plant preferably operating in the solids fermentation process. For the digestion of lignin-containing sustainable raw materials, a device for saturated steam treatment of straw bales or loose lignocellulose-containing material is described in detail. This saturated steam treatment operates batchwise with very energy-rich steam from 20 to 30 bar. A component of this saturated steam treatment is the abrupt pressure release, which is intended to shred the lignocellulose fibers. This principle is generally described in the technical world as "steam explosion". For the subsequent fermentation, reference is preferentially made to solids fermentation, without however excluding a wet fermentation. In contrast to this, in another place reference is explicitly made to the problem of floating layer formation during a wet fermentation of straw. Accordingly, it does not come under consideration for the wet fermentation, since this floats, and result in blocks to outflows and overflows or would wind itself around the paddles or propellers in wet fermentation plants.

The described process from WO2009000305A1 is less suitable on energetic and economic consideration, especially because the batch-operated thermal digestion methods described do not have means for energy recovery from the waste steam from the pressure release. By means of the method described or the plant, the lignocellulose-containing substrate must be transported within the whole plant as a solid. Logistically and particularly in terms of plant engineering, this is considerably more expensive and hence cost-intensive than the transportation of a pumpable suspension, such as is for example present in wet fermentations. Furthermore, no means are present for performing biogas generation from straw in a wet fermentation plant, and the technical problem that straw forms floating layers and is thus not suitable for wet fermentation is even described. A further disadvantage arises from the batch operation of the quasi-continuous dry fermentation in garage fermenters described. On the one hand, methane losses occur during the emptying of the fermenters. In addition, the substantial methane and digester gas emissions thereby arising must be prevented for climate protection and emission legislation reasons, which inevitably entails the enclosure of the whole plant and provision of a waste gas purification system, and decreases the profitability of the whole process.

Outside the technical field of biogas production, in EP0377832A2 a method is described for the treatment of biomass for biological sewage treatment. With the aim of almost complete hydrolysis, the liquid biomass is treated in a thermal pressure hydrolysis, single-stage or multistage, from 150° C. to 300° C. for 30 mins to 120 mins optionally with introduction of additives such as inorganic catalysts. During this, in a heat exchanger, the heat from the hydrolysate is transferred to the biomass to be hydrolyzed. Next, the separation into a solid phase as residue mass and a liquid phase containing monomers as a valuable organic substance is effected.

The method in the patent reference cited, EP0377832A2, concerns neither biogas production nor a fermentation, but rather that of waste water purification by thermal pressure hydrolysis. The stated process parameters are not useful for a subsequent fermentation. Under the conditions described, especially from hemicellulose-containing biomass such as for example straw, not only monomers, but also especially hard to degrade aromatic compounds such as for example HMF and furfurals are formed. These can lead to inhibition of the biological degradation processes. Hence this process is unsuitable for a subsequent fermentation, particularly if a major part of the process liquid is to be recirculated.

Also from another technical field, the use of a biological treatment of lignocellulose-containing substrate with white-rot fungi is known. DE2543939A1 describes a method for increasing the feed value of straw. In this, the straw, pasteurized with steam, is treated with white-rot fungus cultures. These are intended to release the cellulose by predominant lignin degradation and thereby increase the digestibility of the straw. However, in experiments it was found that significant quantities of the cellulose, 20%-35%, were also degraded.

With regard to biogas production from straw, this method is not directly transferable, since the high cellulose losses would inevitably decrease the profitability of the whole process.

The use of a biological treatment of lignocellulose-containing substrate with white-rot fungi in connection with an anaerobic biogas fermentation is described in DE4414459A1. The method focuses primarily on the multistage biogas generation from wastes also containing organic substances, such as domestic refuse or the like, and the mineralization and hygienization accompanying this. As one possible version of the process, lignin degradation in an aerobic stage upstream of the hydrolysis, which is intended to improve subsequent anaerobic cellulose degradation, is described. This lignin degradation should take place through the establishment of a pH from 4.2 to 4.6 and through use of added white-rot fungi, without significant degradation of cellulose or other readily degradable substrate.

The method described in DE4414459A1 is not directly transferable to utilization of mainly lignocellulose-containing biomass. No practical solution to the formation of floating layers, such as is especially to be expected in the processing of straw, is demonstrated. Rather, it is assumed that through the establishment of a DS content of preferably 15% to 20% in the fermenter, no segregation takes place, which is demonstrably not the case with a straw suspension. A further disadvantage comprises the intended introduction of readily degradable organic material such as for example molasses and/or sewage sludge for homogenization of the process, whereby which the process described deviates considerably from a more demanding lignocellulose-based fermentation.

The tendency to form floating layers in the fermentation of lignocellulose-containing material is well-known. This tendency is attributed to the wax layer enclosing the fibers, which prevents the penetration of moisture into the lignocellulose fibers. For elimination of floating layers during the anaerobic fermentation, mechanical methods are known, which destroy or break up the floating layer with stirrers or jet stirrer devices, or by induced flow prevent formation of a floating layer. Such a device is described in DE7901636U1 for liquid manure silos in agricultural operations. In this device, floating layers which can in part be formed from floating straw are collected together with liquid manure in a side-chamber by means of an overflow, and completely destroyed during the subsequent forced transport back into the fermenter by a pump equipped with shredding tools.

A disadvantage in this solution, as also with use of special stirrers, is the abatement of the floating layers with use of conveying or stirring machinery requiring maintenance and additional, often significant, energy consumption associated therewith. Thereby, the problem, but not the actual cause of the formation of the floating layers, is combatted.

WO2006/042551 relates to a method and an apparatus for converting organic wastes into biogas. The organic wastes to be processed are especially dung or animal body wastes, but plant wastes are also considered as biomaterial. In the process described, firstly a fermentation of the organic waste in a first reactor is provided, followed by a hydrolysis of the thus fermented organic waste in an anaerobic hydrolysis tank, followed by a further fermentation in a second reactor.

Problem and Solution

It is common to previously known methods for biogas production from lignocellulose-containing biomass that they may be possible for processing fiber-containing substances such as whole maize plants, but owing to very high plant and/or operating costs are unsuitable or less economic for processing of highly lignified material such as for example straw as the main substrate or in a mono-fermentation of straw.

Existing methods from other technical fields for the utilization of lignocellulose-containing biomass do not meet the specific requirements of biogas production and are not directly transferable or too cost-intensive in their original process form.

The present invention was therefore based on the problem of providing a particularly energy and resource-saving and hence cost-efficient method, with low $CO_2$ emissions, for producing biogas from lignocellulose-containing biomass and a plant for implementing this method. To solve this problem, the invention provides a method according to claim 1 and a plant according to claim 14. Advantageous further developments are mentioned in the dependent claims. The wording of all claims is incorporated by reference into the description.

DESCRIPTION OF THE SOLUTION

The energy and resource-saving production of biogas by anaerobic fermentation of lignocellulose-containing biomass is only possible when the biogas yield is sufficiently high. On the one hand because only then is the energy yield in the form of biogas correspondingly high. Additionally however, especially also because at the same time so much dry substance is degraded that the process water requirement for the mixing of the straw from the solid-liquid separation of the fermentation residue can be almost entirely or even completely covered. This is possible with appropriate pretreatment of the lignocellulose-containing biomass, especially in the form of straw, in several process steps with subsequent wet fermentation of a prepared straw suspension, in several subsequent stages if desired, of an anaerobic fermentation adequately supplied with nutrients, in combination with energy-efficient thermal digestion and with an aerobic biological lignin degradation if desired.

Specifically, with the integrally combined solution concept according to the invention, the following advantages could be attained:

Through the shredding of the lignocellulose-containing biomass such as for example straw, grasses, wood or other agricultural and forestry wastes in the range from 1 mm to 10 mm particle size, the ratio between the energy expenditure for the shredding and the yield of biogas is optimal.

By brief conditioning of the shredded lignocellulose-containing biomass such as for example straw at ca. 80° C. in a moist/humid environment, formation of floating layers in the anaerobic fermentation process is greatly reduced or even completely avoided.

Through physical and thermal treatment of lignocellulose-containing biomass at a temperature of 130-200° C. and subsequent fermentation, the biogas yield is significantly increased and the availability of nitrogen improved.

Through the selection of the temperature up to 200° C., the ratio between the energy expenditure for the physical and thermal treatment and the achievable additional yield of biogas is particularly economical.

Through the adjustment of the content of macro and micronutrients in the fermentation system, the invention provides as an essential core element the means for a mono-fermentation of lignocellulose-containing biomass such as for example wheat straw as monosubstrate. In this, the formation of biogas is considerably improved especially through adjustment of the sodium content, if desired by introduction of sodium hydroxide solution or sodium salts such as for example sodium hydrogen carbonate, in the whole fermentation system to about 100 mg/l to 5,000 mg/l, preferably from 400 mg/l to 2,000 mg/l. Likewise, through adjustment of the content of ammonium nitrogen, if desired by introduction of for example ammonium salts such as ammonium hydrogen carbonate or other nitrogen-containing substances, in the whole fermentation system to about 200 mg/l to 2,000 mg/l, preferably 500 mg/l to 1,200 mg/l, a stabilization and further improvement of biogas formation is achieved.

Through the high degree of recycling of process water from the solid-liquid separation to the fermentation residue treatment for mixing, the requirement for additional macro and micronutrients, especially of sodium and nitrogen, can be markedly reduced or even entirely avoided.

In addition, the possibility exists of further reducing the dry substance content of fermentation wastes arising, through an aerobic fermentation with fungi and with repeat fermentation of the fermentation wastes thus treated to produce additional biogas and finally to increase the process water recycle through the further dry substance degradation associated with this.

Through a combination of the aforesaid measures, the dry substance degradation associated with the anaerobic degradation to biogas is so high that a recycling of process water from the solid-liquid separation can almost entirely or completely cover the liquid requirement during the mixing.

In one embodiment, the method according to the invention for producing biogas from lignocellulose-containing biomass, preferably from straw, is configured as a process with only one fermentation stage, which comprises the following steps:

a) Mixing the lignocellulose-containing biomass with an average particle size smaller than 200 mm, preferably smaller than 20 mm, with aqueous solutions at a temperature of 60-100° C., especially 70-85° C., especially with process water and/or with the aid of steam;

b) Heating the lignocellulose-containing biomass at 130-200° C., preferably 150-180° C., and residence of the thus heated lignocellulose-containing biomass for a duration of 5-120 mins, preferably 10-30 mins, advantageously in a continuous flow reactor space for thermal digestion c) Anaerobic fermentation of the heat-treated lignocellulose-containing biomass by means of microorganisms and recovery of the biogas formed.

In an alternative embodiment, the method according to the invention for producing biogas from lignocellulose-containing biomass, preferably from straw, is configured as a process with two fermentation stages, which comprises the following steps:
a) Mixing the lignocellulose-containing biomass with an average particle size smaller than 200 mm, preferably smaller than 20 mm, with aqueous solutions at a temperature of 60-100° C., especially 70-85° C., especially with process water and/or with the aid of steam;
a1) Anaerobic fermentation of the admixed lignocellulose-containing biomass by means of microorganisms and recovery of the biogas formed;
b) Heating the lignocellulose-containing biomass at 130-200° C., preferably 150-180° C., and residence of the thus heated lignocellulose-containing biomass for a duration of 5-120 mins, preferably 10-30 mins, advantageously in a continuous flow reactor space for thermal digestion
c) Anaerobic fermentation of the heat-treated lignocellulose-containing biomass by means of microorganisms and recovery of the biogas formed.

The configuration of the method as a process with two anaerobic fermentation steps leads to especially high yields of biogas.

From one preferred embodiment of the method according to the invention, the method comprises a heat exchange operating on the countercurrent principle between the admixed lignocellulose-containing biomass from step a) and the heat-treated lignocellulose-containing biomass from step b), in order to enable energy-efficient attainment of the operating temperature of the thermal digestion. A preferred embodiment of the method according to the invention therefore comprises the following steps:
a) Mixing the lignocellulose-containing biomass with an average particle size smaller than 200 mm, preferably smaller than 20 mm, with aqueous solutions at a temperature of 60-100° C., especially 70-85° C., especially with process water and/or with the aid of steam;
a2) Implementation of a heat exchange operating on the countercurrent principle between the lignocellulose-containing biomass obtained in step a), especially after prior adjustment of the dry substance content to 7-20 wt. %, and the heat-treated lignocellulose-containing biomass obtained in step b).
b) Heating the lignocellulose-containing biomass at 130-200° C., preferably 150-180° C., and residence of the thus heated lignocellulose-containing biomass for a duration of 5-120 mins, preferably 10-30 mins, advantageously in a continuous flow reactor space for thermal digestion
c) Anaerobic fermentation of the heat-treated lignocellulose-containing biomass by means of microorganisms and recovery of the biogas formed.

Preferably this heat exchange operating on the countercurrent principle takes place such that subsequent heating by less than 20° K enables energy-efficient attainment of the operating temperature of the thermal digestion in step b).

In an alternative preferred embodiment, the method according to the invention is configured such that it comprises the following steps:
a) Mixing of the lignocellulose-containing biomass with an average particle size smaller than 200 mm, preferably smaller than 20 mm, with aqueous solutions at a temperature of 60-100° C., especially 70-85° C., especially with process water and/or with the aid of steam;
a1) Anaerobic fermentation of the admixed lignocellulose-containing biomass by means of microorganisms and recovery of the biogas formed;
a2) Implementation of a heat exchange operating on the countercurrent principle between the lignocellulose-containing biomass obtained in step a), especially after prior adjustment of the dry substance content to 7-20 wt. %, and the heat-treated lignocellulose-containing biomass obtained in step b).
b) Heating of the lignocellulose-containing biomass at 130-200° C., preferably 150-180° C., and residence of the thus heated lignocellulose-containing biomass for a duration of 5-120 mins, preferably 10-30 mins, advantageously in a continuous flow reactor space for thermal digestion
c) Anaerobic fermentation of the heat-treated lignocellulose-containing biomass by means of microorganisms and recovery of the biogas formed.

Preferably this heat exchange operating on the countercurrent principle takes place such that a subsequent heating by less than 20° K enables energy-efficient attainment of the operating temperature of the thermal digestion in step b).

In the sense of the present invention, lignocellulose-containing biomass should be understood to mean especially a biomass which has lignin, hemicellulose and cellulose as essential components, especially in the form of straw, especially cereal straw, wood and/or grasses.

Below, the integrated solution principle for producing biogas from lignocellulose-containing biomass is explained taking as the example cereal straw, hereinafter named straw, without a limitation thereby being intended. For those skilled in the art, the technical means and operating principles are of course readily transferable and applicable to other types of lignocellulose-containing biomass such as for example grasses, woods or mixed substrates. Their transfer is therefore not explicitly described. It is also self-evident that the method described and the plant are also in principle suitable for biogas generation together with proportions of non-lignocellulose-containing biomass such as for example liquid manure.

The percentage data stated in the description are, unless explicitly otherwise stated, to be interpreted as contents by mass.

The straw is as a rule firstly delivered in square bales with a dry substance content from 80% to 95% and freed of foreign matter. For energy reasons, the mechanical shredding of the straw is effected in several stages. Firstly, the straw bales are mechanically broken up and the straw if required preshredded to a particle size smaller than 200 mm. The subsequent shredding to a particle size of preferably 1 mm to 10 mm is especially favorable for the process and can for example be effected in a hammer-mill, a chopper or a shredder. In special cases, shredding to meal with a particle size <200 μm can be useful in order significantly to increase the substrate surface area through this physical mechanical digestion.

Next, the straw is subjected to a heat treatment to destroy the wax layer. The shredded straw is impacted by hot water and/or steam in a steamer with integrated mixer so that the straw thus moistened reaches a temperature from 60° C. to 100° C., preferably 70° C. to 85° C. Thereby, the wax layer of the lignocellulose fibers of the straw is adequately destroyed, as a result of which the water uptake is improved and thereby the formation of floating layers during the later fermentation is prevented. A significant decrease in the stirring power necessary and thus an energy saving during the fermentation thereby become possible. After a residence time from 0.5 mins to 30 mins, preferably 5 mins to 15 mins, the moistened straw is discharged with a dry substance content from 20% to 60%, preferably ca. 30%. If hot water is used in this sub-process, then this can preferably be liquid recovered in-process, which is fed into the steamer directly or after heating, especially after heating with waste heat available in-process. Moreover, introduction of enzymes such as for example lignin-modifying enzymes, glucanases, hemicellulases and pectinases into the steamer is possible in order to effect a first degradation of the lignocellulose-containing biomass.

After the straw has been moistened, there is the possibility of an aerobic biological treatment with fungi or alternatively with enzymes for specific lignin degradation and, associated therewith, better availability of cellulose and hemicellulose in the subsequent anaerobic fermentation. The pasteurizing effect of the preceding heat treatment is advantageous for the biological treatment. If fungi are added, this takes place with adjustment, as a rule with lowering, of the pH to ca. 3.5 to 8, especially to 4 to 6, for example by introduction of acids. Especially suitable as lignin-cleaving or degrading fungi are Basidiomycete strains, *Pleurotus ostreatus, Phellinus torulosus, Coriolus hirsutus, Trametes hirsuta, Cyathus helenae, Cyathus olla, Coprinus comatus, Cyathus limbatus, Polyporus adustus, Chyrosporium lignorum* and *Peniophora crema* and strains thereof especially adapted for primary lignin digestion/degradation instead of cellulose and hemicellulose degradation or enzymes thereof. The introduction of the fungi can for example be effected with aqueous cultures under suitable conditions for this. The aerobic degradation takes place with the introduction of suitable quantities of oxygen, preferably in the form of air, especially moist air. As apparatus, especially chambers and aerobic containers with gas input near the bottom or ventilated hoses with large cross-sections can be used. Suitable hoses, such as are for example known from silaging, can be stored on open areas or in sheds and made with gas supply tubes/lances with gas outlet openings or gas inlets for example in the form of nozzles mounted in the hose bottom and outlet openings on the hose upper side, preferably as a pressure relief valve, in order to ensure effective fresh gas circulation for the fungal growth. The temperature here should be from ca. 10° C. to 40° C., preferably from 15° C. to 35° C. As the residence time, 1-4 weeks, especially ca. 1-2 weeks is preferred for the case where the priority is to achieve additional liberation of cellulose and hemicellulose with the fungi and enzymes thereof for the biogas generation instead of the lignin degradation. These values should be regarded as guide values and dependent on the particular fungal species, the substrate and its degree of shredding and additives used, especially enzymes. By controlling the oxygen and carbon dioxide content, and if desired the addition of inhibitors inhibiting the cellulose and/or hemicellulose degradation, the loss of readily fermentable substrate can be prevented and/or the growth of competing microorganisms retarded.

Alternatively or in addition, enzymes for enzymatic digestion can also be added to the moistened straw. Suitable for this are enzymes such as for example lignin-modifying enzymes, ligninases, especially laccases and glucanases and pectinases. With use of enzymes, the dry substance content of the moist straw should be selected such that free water is present. The duration of action of the enzymes is from 1-24 hrs, preferably 2-6 hrs, at a temperature from 5-80° C., preferably 20-50° C. and a pH from 2-10, preferably 5-8. For optimal action of the enzymes, continuous or discontinuous mixing of the substrate for example in a stirred vessel is advisable.

The moistened, and if desired also biologically and/or enzymatically treated, straw is mixed with water, preferably with recycled process water, to give a pumpable, fermentable suspension. The mixing of the moist straw with water can take place in a mixer, for example however also in an eccentric screw pump. Here, for the subsequent wet fermentation of this suspension, a dry substance content from 5% to 30%, preferably 10% to 18%, has been found especially suitable. By adjustment of the temperature of the recycled process water, the temperature of the suspension can be adjusted such that the fermentation temperature of the subsequent anaerobic fermentation is maintained in the intended optimal range. Alternatively, the conditioning of the suspension and hence of the subsequent fermentation can also be effected via indirect heat exchange in a heat exchanger, for example a plate heat exchanger or a tube bundle device, with utilization of waste heat streams or cooling water if desired.

In some cases, it can be useful further to shred the lignocellulose-containing biomass mixed in the suspension, especially if the average substrate particle size is greater than 2 mm. This can for example be achieved with a wet shredding by means of a wet mill or cutting wheels in the pipe transport system or disperser. If required, the wet shredding can also be performed in several stages. It can advantageously be installed directly after the mixing, but also after the heat exchanger directly before the anaerobic fermentation.

The resulting suspension is subjected to an anaerobic fermentation in one or more fermenters, together with nitrogen sources such as such as for example ammonium salt and/or with additives, especially macro and micronutrients such as sodium and/or phosphorus and/or zinc compounds. Usually, the fermentation takes place continuously or with pulsed introduction of substrate into several fermenters at least quasi-continuously. The fermenter or fermenters should be equipped with at least one stirring device in order to ensure adequate homogenization of the fermenter contents and to improve mass transport.

Surprisingly, it was found in fermentation experiments that adjustment of the ammonium content in the whole fermentation system to 200 mg/l to 2,000 mg/l, preferably 500 mg/l to 1,200 mg/l, stabilizes the degradation process and considerably improves biogas formation.

Furthermore, in long-term degradation experiments it was surprisingly found that through the adjustment of the sodium content in the whole fermentation system to about 100 mg/l to 5,000 mg/l, preferably to 400 mg/l to 2,000 mg/l, biogas formation is considerably increased. The adjustment of the sodium content can be effected with various sodium carbonates, sodium hydroxide solution or also other sodium-containing organic substances or wastes. For this, the introduction of the sodium-containing substance does not inevitably have to take place directly into the suspension or directly into the fermenter, but rather the optimal sodium content can also be adjusted indirectly via the recycled process water.

Furthermore, the introduction of macro and micronutrients such as for example potassium, calcium, magnesium, di- and trivalent iron and trace elements such as for example cobalt, copper, molybdenum, nickel, selenium and tungsten and compounds thereof and of vitamins can have a beneficial effect on the metabolism of the microorganisms and hence on the biogas yield.

Microorganisms, especially those which carry out a hydrolysis, acidogenesis, acetogenesis and methanogenesis are used. The residence time of the anaerobic fermentation is selected such that a stable microorganism population is established in the fermenter. With mesophilic or thermophilic operation, a residence time from 10 to 50 days, preferably 15 to 30 days, is advantageous. The biogas generated is collected and taken off for further processing.

After the lignocellulose-containing biomass has been at least in part fermented to biogas in the first fermentation step, the solids-containing outflow from the fermentation is fed into a continuously operating thermal digestion. In another process system, there also exists the possibility of feeding the fermentable suspension directly into the thermal digestion without prior anaerobic fermentation, and feeding the digested suspension into an anaerobic fermentation.

Surprisingly, it was found in experiments that such digestion, even without sudden pressure release, destroys the fiber bonding of the lignocellulose structure so far that previously non-degradable organic components, especially further cellulose and hemicellulose, are rendered accessible for the aerobic degradation in industrially significant quantities. As a result, the biogas yield is significantly increased. For this, the pumpable outflow is conveyed into the pressurized digestion system with a suitable pump, for example an eccentric screw pump, in that firstly a two-stage heating, then a thermal digestion, and finally a one or two-stage cooling, takes place.

The first stage of the heating of the outflow takes place in that heat from hot, already digested outflow is indirectly transferred in such a manner that the temperature of the then heated outflow lies at most 20 K, preferably at most 10 K, below the intended digestion temperature. The remaining heating takes place in the second stage through indirect heat transfer from a heat transfer medium, such as for example steam, water or thermal oil or by direct steam, to the intended digestion temperature. The thermal digestion advantageously takes place at 130° C. to 200° C., preferably at 150° C. to 170° C. By means of a digestion reactor in the form of a pressure vessel, an average residence time of the outflow at this digestion temperature from 5 mins to 60 mins, preferably from 10 mins to 30 mins is achieved. For homogenization and for avoidance of short circuit flows, the digestion reactor can be equipped with a stirring device or other mixing units. Next, the digested outflow is indirectly cooled with the outflow to be heated, and if desired further indirectly or directly cooled in a second heat exchanger, in order finally to be fed into a further anaerobic degradation to biogas. As heat exchangers, for example pressure-resistant plate heat exchangers or tube bundle devices can be utilized.

Advantageous in this design is the reduction of the mass flow to be heat treated compared to direct thermal digestion of the straw before the first fermentation. In conjunction with the continuously operating digestion system and the internal heat transfer described, the energy requirement is significantly decreased compared to conventional digestion methods for the treatment of lignocellulose-containing biomass. Through an increase in the DS content of the outflow by partial solid-liquid separation and enrichment of the remaining outflow with the recovered solid, the energy efficiency of the digestion system can be further improved. In this, the solid-liquid separation can for example be effected by decanters, centrifuges or presses. Advantageously, the first fermentation and/or the solid-liquid separation is operated such that the DS content of the outflow to be heat treated lies in the range from 7% to 20%, especially preferably in the range from 9% to 13%. A liquid phase arising in the solid-liquid separation is recycled within the process, preferably for the mixing of moistened straw, after interim storage if desired.

The anaerobic degradation of the heat-treated outflow is effected by recycling into the first fermentation together with fresh substrate or preferably by feeding into a further, second fermentation. The latter can be operated mesophilically and also thermophilically, whereby the temperature can in every case be maintained through the influx of treated outflow. Energy advantages can arise with the implementation of a thermophilic fermentation, since the waste heat from the digestion can be used for the heating, and, in the further course of the process, process liquid with a higher temperature can be recycled into the first fermentation. Advantageously, the second fermentation is also operated such that the microorganism population is kept in a productive, steady state. This is ensured with a residence time from 5 to 15 days. The technical implementation of the second fermentation can be effected in the same manner as with the first fermentation.

In the case of recycling of digested outflow back into the first fermentation (single-stage fermentation), a part of the solid substance recovered in the solid-liquid separation must be discharged from the system. Via this release, the non-degradable lignin and mineral components are discharged from the system. This mass flow is available as raw material for later use of the lignin as such and/or directly or after further treatment as organic fertilizers for agriculture.

The outflow from the second fermenter can be used as organic fertilizer or is preferably separated by a solid-liquid separation into a liquid and a solids-containing phase. The solids-containing phase can partially be recycled into the second fermentation in order to increase the volume loading and prolong the solids residence time and hence to increase the biogas yield. With a further increase in the biogas yield, the dry substance to be discharged from the overall process further decreases, as a result of which cost savings arise in in relation to logistics.

The portion of the solids-containing phase to be discharged analogously to the singe-stage fermentation can for example be used as a lignin source or also as organic fertilizer. With use as organic fertilizer, the supply of both humus and also nutrients, especially the supply of the agricultural farmland or the plant cultivation taking place thereon with potassium, nitrogen and phosphorus, can be considerably improved. If the anaerobically non-degradable organic substance (mainly the lignin) is applied onto the appropriate farmland from which the straw has previously been entirely removed for biogas production, the humus balance can be completely compensated.

The liquid phase recovered in the solid-liquid separation is recycled in-process, preferably into the mixing of the straw before the first fermentation. As a result, the water consumption can be significantly reduced or even entirely covered in-process. This also applies especially for mainly solids-containing substrates such as for example straw, since through the proposed method the biogas yield and associated therewith the dry substance degradation is significantly increased, as a result of which the liquid losses due to the biogas formation itself and due to the discharge of the solids-containing phase can be almost entirely or completely compensated by the moisture of the substrate. Furthermore, the recycling of the liquid phase effects a recycling of macro and micronutrients such as for example nitrogen and sodium and to some extent also of active microorganisms themselves. This leads on the one hand to a stabilization of the process and on the other to a decrease in the introduction of additives, as a result of which the profitability of the whole process is improved.

For recovery of valuable substances contained in the liquid phase, such as for example potassium compounds or dissolved lignin components or for removal of contaminants, a treatment of the liquid phase can be performed before the recycling. Suitable treatment methods can for example be membrane methods, filters and/or selective precipitations, evaporation or an aerobic treatment.

In addition, there is the possibility of subjecting the second outflow or the solids-containing phase obtained after complete or partial phase separation to a biological after-treatment with lignin-degrading fungi analogously to the previously described treatment of the straw before the first fermentation. As a result, further solids can be degraded, as a result of which the solid matter (fertilizer) to be transported away is further reduced in quantity and still more process liquid can be generated. Further, with recycling of the outflow thus treated or the solids phase thus treated into the fermentation, a further biogas yield becomes possible, as a result of which the efficiency of the whole process is increased.

While all previously known methods and/or plants for fermenting lignocellulose-containing biomass to biogas could not become established because of their low profitability, the generation of biogas from precisely such lignocellulose-containing biomass as the main substrate or even as mono-substrate is economically possible with the solution described.

The proposed solution improves the ratio of process energy consumption to biogas yield significantly compared to known methods and through the optimized process water recovery and recycling it leads to considerable improvements with regard to water consumption and additive usage and hence to marked economic improvements.

BRIEF DESCRIPTION OF THE DIAGRAMS

DETAILED DESCRIPTION OF PREFERRED EMBODIMENTS

The practical examples of the invention are shown in the diagrams and are described in more detail below.

Practical Example 1

Figure 1:
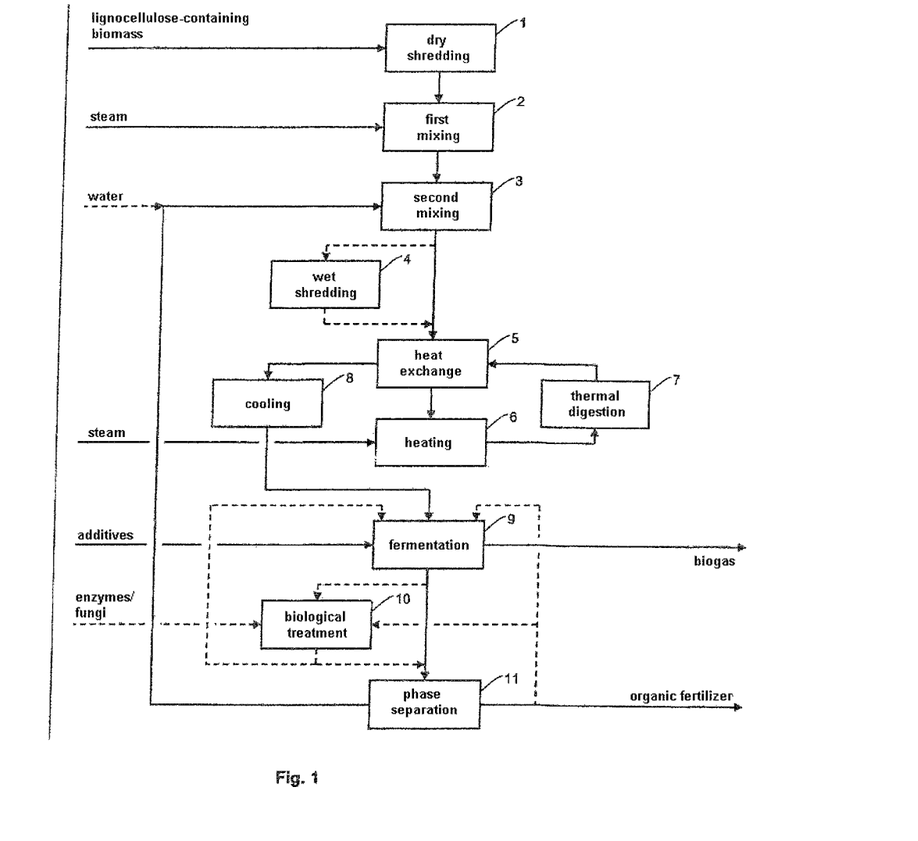
FIG. 1 shows a diagrammatic representation of one embodiment of a single-stage method for producing biogas from lignocellulose-containing biomass according to the invention.

FIG. 1 shows a diagrammatic example of a single-stage method for producing biogas from lignocellulose-containing biomass such as for example straw or wood according to the invention.

The loose or compressed lignocellulose-containing biomass is, after cleaning from stones and other foreign bodies if desired, firstly passed to the dry shredding 1. In a shredder, a chopper or a hammer-mill, the lignocellulose-containing biomass is shredded to a substrate particle size smaller than 200 mm, preferably smaller than 20 mm, and for straw especially preferably to a substrate particle size from 1 mm to 10 mm. Alternatively or in addition, a treatment in a wet shredder can be effected.

Next, the shredded substrate is conveyed, for example pneumatically, into the first admixture 2. The first admixture 2 is in the form of a steamer, mixer, stirrer or circulator. In this apparatus, the shredded substrate is impacted with hot water and/or steam, in order to heat it to 60-100° C., preferably to 70-85° C., for a duration of 0.5 mins to 30 mins, preferably 5 mins to 15 mins. Through the elevated temperatures, degassing of the substrate is effected and the water uptake capability improved, in that especially detachment of the wax layer occurs. Through the water uptake of the substrate, the density of the particles increases, as a result of which floating layer formation in the fermentation 9 is reduced or even completely prevented. In the first admixture 2 a moistened substrate with a DS content from 20% to 60%, preferably ca. 30%, is generated.

The substrate moistened by the first admixture 2 is mixed together with water in the second admixture 3 to give a suspension with a DS content from 5% to 30%, preferably from 10% to 18%. For the mixing, process waters from the phase separation 11 are used, through which the fresh water requirement can be almost entirely or even completely covered. In addition, nutrients, trace elements and microorganisms are recycled with the recycled process water.

Further, in some embodiments it can be useful further to shred the substrate mixed in suspension, especially when the average substrate particle size is greater than 2 mm. This can be achieved with a wet shredding 4 for example with a wet mill.

The pumpable suspension is fed into a continuously operating thermal digestion 7, in order to break up the fiber bonding of the lignocellulose structure and also to make less easily degradable components accessible for efficient anaerobic degradation. The transport into the thermal digestion 7 operating under pressure can for example be effected with an eccentric screw pump. The heat exchanger 5 and the heating 6 and also the condenser 8 are also operated under a pressure such that no water vapor arises from the suspension. The thermal digestion 7 takes place in the aqueous phase at a temperature from 130° C. to 200° C., preferably at a temperature from 150° C. to 170° C. In order to minimize the energy consumption of the thermal digestion, indirect heating of the suspension is first effected in a heat exchanger 5 preferably operating in countercurrent. Thereby, heat is transferred from the already heat-treated hot suspension to the suspension still to be treated. During this, the heat exchanger 5 transfers so much heat that the temperature of the heated suspension lies at most 20K, preferably at most 10K below the desired digestion temperature. Next, the further heating up to the digestion temperature in the heater 6 is effected with steam. This can take place indirectly for example in a plate heat exchanger or by injection of direct steam. Finally, the hot suspension flows into the digestion reactor (thermal digestion 7). In this insulated pressure vessel, a residence time from 5 mins to 60 mins, preferably 10 mins to 30 mins at the appropriate digestion temperature is achieved. To improve the flow behavior, the digestion reactor can be equipped with a stirrer or another mixing or conveying device.

The hot digested suspension again passes through the heat exchange 5 in order to give up the heat to the suspension still to be treated. After this, the digested suspension is conditioned in the cooler 8, which for example operates with cooling water, such that the temperature of the fermentation 9 is kept in a temperature range suitable for the meso or thermophilic anaerobic degradation.

The resulting suspension, if desired together with additives, is fed into an anaerobic fermentation 9. Additives can be nitrogen sources for example in the form of ammonium hydrogen carbonate and/or macro and micronutrients such as for example sodium and/or phosphorus and/or zinc compounds and/or commercial trace element solutions. The fermentation 9 can comprise one or more parallel operated fermenters, which are preferably equipped with a stirrer and advantageously operated quasi-continuously by means of a pulsed substrate feed. Through the fermentation following the thermal digestion, the overall yield of biogas within economic residence times is markedly increased. The residence time of the mesophilic or thermophilic anaerobic fermentation 9 is preferably 10 to 30 days. The continuously generated biogas is drawn off in the upper part of the fermenter or fermenters and passed via a manifold for further processing.

The outflow from the fermentation 9 only still contains very poorly degradable fiber components, which largely consist of lignin. Because of the minerals content and the organic components still contained the outflow can be very well utilized as organic fertilizer. Preferably however, the outflow is firstly passed to a phase separation 11 and separated into a liquid and a solids-containing phase. This solid-liquid separation can for example be effected by means of a decanter. In this case, a semi-solid, readily storable solid phase with scarcely any or absolutely no free water present is produced. The solids-containing phase can be partially fed back into the fermentation in order to further increase the yield. As a result, a higher solids residence time is achieved and the biogas yield increased. The excess content of the solids-containing phase can, after interim storage if desired, be used in agriculture as organic fertilizer. Thereby, the humus balance and minerals supply to the agricultural areas can be considerably improved and sustainable management ensured.

The liquid phase generated in the phase separation 11 is fed back into the second admixture 3 as process water, if desired after interim storage. Through the effective degradation of the substrate to biogas, so much DS is simultaneously degraded that much process water is generated in the phase separation 11, as a result of which the water consumption of the overall process of biogas generation from lignocellulose-containing biomass is particularly low. The recycled quantity of process water can be so great that absolutely no fresh water now has to be fed into the mixing.

In order to make still further organic substance available for the anaerobic degradation and thus further to increase the biogas yield and/or to reduce the quantity of the solids-containing phase arising and/or to increase the yield of recovered process water, the outflow from the fermentation and/or the solid recovered from the phase separation can be fed into a biological treatment 10. By addition of enzymes and/or fungi a biological digestion can be achieved, whereby especially cellulose and hemicellulose become more easily accessible for anaerobic degradation processes, and with recycling of the stream thus treated into the anaerobic fermentation 9 can be converted to biogas. With the use of enzymes only, the DS content of the moistened substrate should be selected such that free water is present. In this case, an aerobic environment is not always absolutely necessary. The introduction of one or more enzyme solutions can be effected substrate-specifically with metering pumps. For optimal action of the enzymes, continuous or discontinuous mixing of the substrate for example in a stirred vessel is advantageous. The duration of action of the enzymes is from 1-24 hrs, preferably 2-6 hrs, at a temperature from 5-80° C., preferably 20-50° C. and a pH from 2-10, preferably 5-8. If the biological treatment is effected with fungi, this occurs with adjustment, as a rule with lowering, of the pH to ca. 3.5 to 8, especially to 4 to 6, for example by introduction of an acid. The introduction of the fungi is effected for example in a controlled manner in the form of a pumpable cell suspension. As the reaction space, for example an aerated aerobic reactor is possible. In addition, the biological treatment 10 with direct use of the outflow from the fermentation 9 can also be effected as an aerobic submerged culture. For this, the outflow can be passed into a continuously or discontinuously operating aerated aerobic reactor containing the lignin-degrading fungi. Alternatively, storage of the moistened substrate treated with a fungal suspension can be effected in several aerated tubular reactors, which enable quasi-continuous operation of the overall process. The temperature here should be from ca. 10° C. to 40° C., preferably in the range 15 to 35° C. As the residence time for one, ca. 1-4 weeks, especially ca. 1-2 weeks, are preferred.

Depending on the objective, the stream emerging from the biological treatment 10 is fed back into the fermentation 9 and/or fed into the phase separation 11.

Practical Example 2

Figure 2:
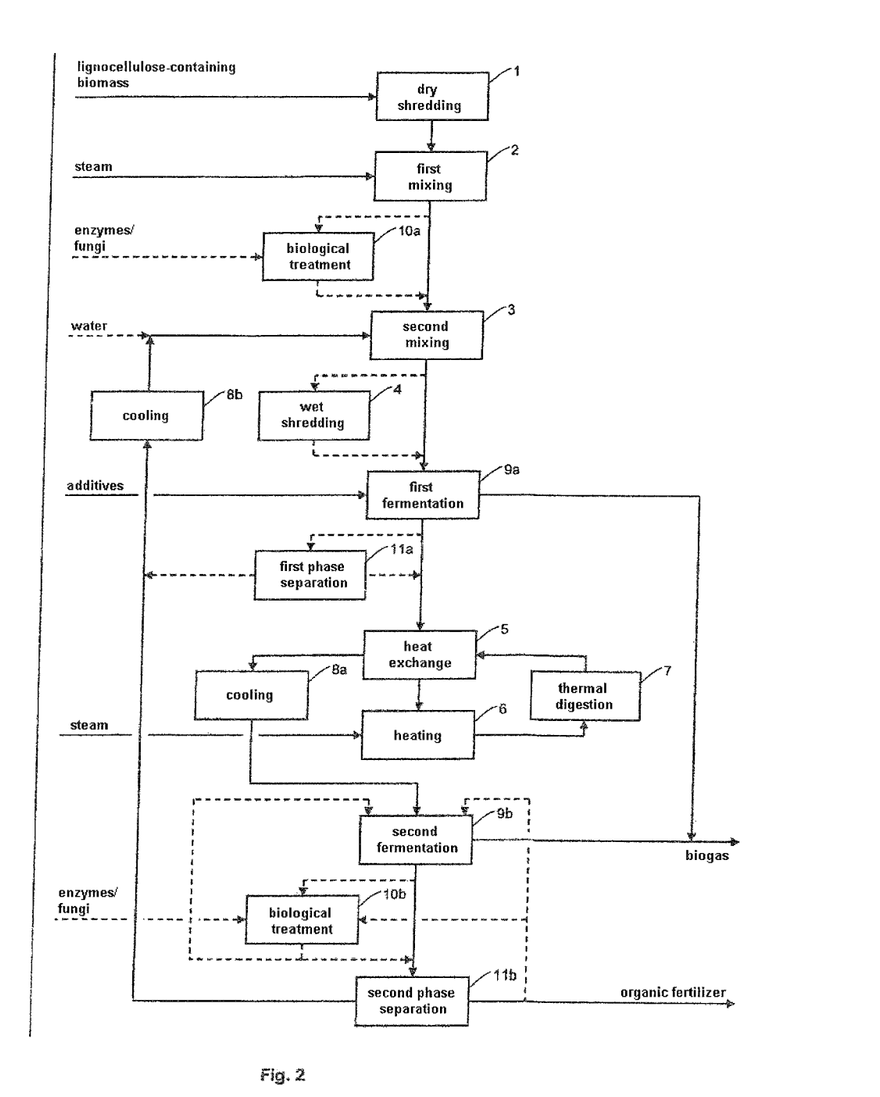
FIG. 2 shows a diagrammatic representation of one embodiment of a multistage method for producing biogas from lignocellulose-containing biomass according to the invention.

FIG. 2 shows a diagrammatic example of a multistage process for producing biogas from lignocellulose-containing biomass such as for example straw or wood according to the invention.

The loose or compressed lignocellulose-containing biomass is, after cleaning from stones and other foreign bodies if desired, firstly passed to the dry shredding 1. In a shredder, a chopper or a hammer-mill, the lignocellulose-containing biomass is shredded to a substrate particle size smaller than 200 mm, preferably smaller than 20 mm, and for straw especially preferably to a substrate particle size from 1 mm to 10 mm. Alternatively or in addition, a treatment in a wet shredder can be effected.

Next, the shredded substrate is conveyed, for example pneumatically, into the first admixture 2. The first admixture 2 is executed as a steamer, mixer, stirrer or recycler. In this device, the shredded substrate is impacted with hot water and/or steam, in order to heat it to 60-100° C., preferably to 70-85° C., for a duration of 0.5 mins to 30 mins, preferably 5 mins to 15 mins. Through the elevated temperatures, the degassing of the substrate is effected and the water uptake capability improved, in that especially detachment of the wax layer occurs. Through the water uptake of the substrate, the density of the particles increases, as a result of which floating layer formation in the fermentation 9 is reduced or even completely prevented. In the first admixture 2 a moistened substrate with a DS content from 20% to 60%, preferably ca. 30%, is generated.

In one embodiment, there is the possibility of a biological treatment 10a of the moistened substrate, which was pasteurized by the high temperatures in the first admixture 2. By addition of enzymes and/or fungi a biological digestion can be achieved, as a result of which especially cellulose and hemicellulose become more readily available for the subsequent anaerobic fermentation. With the use of enzymes only, the DS content of the moistened substrate should be selected such that free water is present. In this case, an aerobic environment is not always absolutely necessary. The introduction of one or more enzyme solutions can be effected substrate-specifically with metering pumps. For optimal action of the enzymes, continuous or discontinuous mixing of the substrate for example in a stirred vessel is advantageous. The duration of action of the enzymes is from 1 to 24 hrs, preferably 2 to 6 hrs, at a temperature between 5-80° C., preferably 20-50° C. and a pH between 2-10, preferably 5-8. If the biological treatment is effected with fungi, this occurs with adjustment, as a rule with lowering, of the pH to ca. 3.5 to 8, especially to 4 to 6, for example by introduction of an acid. The introduction of the fungi is effected for example in a controlled manner in the form of a pumpable cell suspension. As the reaction space, for example an aerated aerobic reactor is possible. Alternatively, the storage of the substrate moistened and treated with a fungal suspension can be effected in several aerated tubular reactors, which enable quasi-continuous operation of the overall process. The temperature here should be from ca. 10° C. to 40° C., preferably in the range to 35° C. As the residence time for one, ca. 1-4 weeks, especially ca. 1-2 weeks, are preferred.

The substrate moistened by the first admixture 2, and also digested by the biological treatment 10a if desired, is mixed together with water in the second admixture 3 to give a suspension with a DS content from 5% to 30%, preferably from 10% to 18%. For the mixing, process waters from the phase separation 11 are used, through which the fresh water requirement can be almost entirely or even completely covered. In addition, nutrients, trace elements and microorganisms are recycled with the recycled process water.

By means of a condenser 8b between the phase separation 11b and the second admixture 3, the recycled process waters can be conditioned such that the temperature of the first fermentation 9a is maintained in a temperature range suitable for the meso or thermophilic anaerobic degradation. In other embodiments, the cooler can also be installed at another position in the process, in order for example to cool the whole liquid stream or the suspension after the second mixer.

Further, in some embodiments it can be useful further to shred the substrate mixed in the suspension, especially when the average substrate particle size is greater than 2 mm. This can be achieved with a wet shredding 4, for example with a wet mill.

The resulting suspension, together with additives if desired, is fed into a first anaerobic fermentation 9a. Additives can be nitrogen sources for example in the form of ammonium hydrogen carbonate and/or macro and micronutrients such as for example sodium and/or phosphorus and/or zinc compounds and/or commercial trace element solutions. The first fermentation 9a can comprise one or more parallel operated fermenters, which are preferably equipped with a stirrer and advantageously operated quasi-continuously by means of a pulsed substrate feed. The residence time of the mesophilic or thermophilic anaerobic fermentation 9a is preferably 10 to 25 days. The continuously generated biogas is drawn off in the upper part of the fermenter or fermenters and passed via a manifold for further processing.

After the lignocellulose-containing biomass has been at least partly fermented to biogas in the first fermentation 9a, the pumpable fiber-containing outflow is fed into a continuously operating thermal digestion 7, in order to render less easily degradable components accessible for a further efficient anaerobic degradation. The transport into the thermal digestion 7 operating under pressure can for example be effected with an eccentric screw pump. The heat exchanger 5 and the heating 6 and the condenser 8a are also operated under a pressure such that no water vapor arises from the aqueous medium. The thermal digestion 7 takes place in the aqueous phase at a temperature from 130° C. to 200° C., preferably at a temperature from 150° C. to 170° C. In order to minimize the energy consumption of the thermal digestion, indirect heating of the fiber-containing outflow is firstly effected in a heat exchanger 5 preferably operating in countercurrent. Thereby, heat from the already heat-treated hot outflow is transferred to the outflow still to be treated. During this, the heat exchanger 5 transfers so much heat that the temperature of the heated outflow lies at most 20K, preferably at most 10K below the desired digestion temperature. Next, the further heating takes the digestion temperature is effected in the heater 6 with steam. This can take place indirectly for example in a plate heat exchanger or by injection of direct steam. Finally, the hot outflow flows into the digestion reactor (thermal digestion 7). In this insulated pressure vessel, a residence time from 5 mins to 60 mins, preferably 10 mins to 30 mins at the appropriate digestion temperature is achieved. To improve the flow behavior, the digestion reactor can be equipped with a stirrer or another mixing or conveying device.

In an energetically particularly advantageous form of the procedure, there is the possibility of increasing the DS content of the outflow reaching the thermal digestion 6. Owing to the lower water content in the fiber-containing stream to be treated, the quantity of heat required for the digestion is reduced. The enrichment of the DS is effected by passing at least one part of the outflow firstly to the phase separation 11a and separating it there into a liquid and fiber-containing phase. This solid-liquid separation can for example be effected by means of a decanter. The fiber-containing phase, after mixing with the untreated part of the outflow if desired, is fed into the thermal digestion 6. The preferred DS content of the outflow conveyed for thermal digestion is 7% to 15%. A recovered liquid phase from the phase separation 11a, after interim storage if desired, is recycled to the second admixture 3.

The hot digested outflow again passes through the heat exchanger 5 in order to give up the heat to the outflow still to be treated. After this, the digested outflow is conditioned in the condenser 8a, which for example operates with cooling water, such that the temperature of the second fermentation 9b is kept in a temperature range suitable for the meso or thermophilic anaerobic degradation.

The digested fiber-containing outflow is fed into a further anaerobic fermentation 9b. Through the further fermentation of the cellulose and hemicellulose now better available for the biogas generation, the overall yield of biogas is markedly increased. The residence time of the mesophilic or thermophilic anaerobic fermentation 9b is preferably 5 to 15 days. The second fermentation 9b can also comprise one or more parallel operated fermenters, which are preferably equipped with a stirrer and advantageously operated quasi-continuously by means of a pulsed substrate feed. The continuously generated biogas is drawn off in the upper part of the fermenter or fermenters and together with the gas from the first fermentation 9a passed via a manifold for further processing.

The outflow from the second fermentation 9b only still contains very poorly degradable fiber components, which largely consist of lignin. Because of the minerals content and the organic components still contained the outflow can be very well utilized as organic fertilizer. Preferably however, this second outflow is firstly passed to a second phase separation 11b and separated into a liquid and a solids-containing phase. This phase separation can also for example be effected with a decanter. In this case, a semi-solid, readily storable solid phase with scarcely any or absolutely no free water present is produced. The solids-containing phase can be recycled into the second fermentation in order further to increase the yield. As a result, a higher solids residence time is achieved and the biogas yield increased. The excess content of the solids-containing phase, after interim storage if desired, can be used in agriculture as organic fertilizer. As a result, the humus balance and minerals supply to the agricultural areas can be considerably improved and sustainable management ensured.

The liquid phase generated in the second phase separation 11b is recycled into the second admixture 3 as process water if desired after interim storage and a condenser (8b). Through the effective degradation of the substrate to biogas, so much DS is simultaneously degraded that much process water is generated in the phase separation 11, as a result of which the water consumption of the overall process of biogas generation from lignocellulose-containing biomass is particularly low. The recycled quantity of process water can be so great that no fresh water whatever now has to be fed into the mixing.

In order to make still further organic substance available for the anaerobic degradation and thus further to increase the biogas yield and/or to reduce the quantity of the solids-containing phase arising and/or to increase the yield of recovered process water, the outflow from the second fermentation and/or the recovered solids from the second phase separation can be fed into a biological treatment 10b. This can preferably be effected with lignin-degrading fungi analogously to the biological treatment 10a. In addition, the biological treatment 10b in case of direct use of the outflow from the second fermentation 9b can also be effected as an aerobic submerged culture. For this, the outflow can be passed into a continuously or discontinuously operating aerated aerobic reactor containing the lignin-degrading fungi. Depending on the objective, the flow emerging from the biological treatment 10b is recycled into the second fermentation 9b and/or fed into the second phase separation 11b.

The invention claimed is:

1. A method for producing biogas from lignocellulose-containing biomass which comprises the following steps:
    a) Shredding the lignocellulose-containing biomass in a hammer-mill to an average particle size in a range of 1-10 mm, wherein the biomass comprises a dry solid (DS) content between 80% to 95% and then mixing for 5-15 min at a temperature between 70° C. and 85° C. with at least one of water, aqueous solutions, and/or steam, wherein the mixing destroys a wax layer of the lignocellulose-containing biomass and results in a mixture containing a moistened lignocellulose-containing biomass with a OS content between 20% and 60%, wherein water is not removed from the mixture containing the moistened lignocellulose-containing biomass and wherein the mixture containing the moistened lignocellulose-containing biomass is further mixed with additional water that comprises recycled process water, resulting in a lignocellulose-containing biomass suspension with a DS content between 5% and 30%, wherein the lignocellulose-containing biomass suspension is pumped into a first anaerobic fermenter without a soaking step;
    b) Fermenting the lignocellulose-containing biomass suspension in the first anaerobic fermenter in a first anaerobic fermentation by means of microorganisms to produce a biogas and recovering the biogas formed during the first anaerobic fermentation;
    c) Heating the lignocellulose-containing biomass suspension as it is obtained in step b) at a temperature between 130° C. and 200° C. to generate a heat-treated lignocellulose-containing biomass suspension, wherein the heating is through direct steam or indirect heat transfer from a heat transfer medium selected from the group consisting of steam, water and thermal oil, wherein the lignocellulose-containing biomass suspension is thermally digested in a digestion reactor for a duration of 10 to 30 minutes to obtain the heat-treated lignocellulose-containing biomass suspension;
    d) Fermenting the heat-treated lignocellulose-containing biomass suspension obtained in step c) in a second anaerobic fermentation by-means of microorganisms to produce a biogas and recovering the biogas formed during the second anaerobic fermentation;
    e) Subjecting an outflow obtained in step d) to a phase separation; and
    f) Obtaining a liquid phase from step e) in the form of process water that is at least in part recycled as the additional water into the further mixing of lignocellulose-containing biomass in step a) and thereby fresh water for mixing is at least considerably reduced or becomes completely unnecessary; and
    g) Obtaining a solid-rich phase in step e) as organic fertilizer; and
    wherein the method further comprises a heat exchanger operation in the countercurrent principle between the incoming lignocellulose-containing biomass suspension obtained in step b) and a portion of the heat-treated lignocellulose-containing biomass suspension that is already heat-treated and obtained from step c) without sudden pressure release to form a preheated suspension, and transferring the preheated suspension to the digestion reactor in step c) for the heat treatment.

2. The method according to claim 1, characterized in that through the heat exchanger operation in countercurrent principle, preheating of the lignocellulose-containing biomass obtained in step b) to a temperature from 110-180° C. takes place.

3. The method according to claim 1, wherein at least one of the first and the second anaerobic fermentation is effected together with an adjustment of a sodium content in the whole fermentation system to 100 mg/l to 5000 mg/l by introduction of sodium compounds.

4. The method according to claim 1, wherein at least one of the first and the second anaerobic fermentation is effected together with an adjustment of an ammonium content in the whole fermentation system to 200 mg/l to 2000 mg/l by introduction of ammonium compounds and/or other nitrogen containing substances.

5. The method according to claim 1, wherein the lignocellulose-containing biomass during and/or after mixing with water realized in step a) is subjected to a biological treatment with enzymes in the presence of water that cellulose and/or hemicellulose components are considerably better available in the subsequent first anaerobic fermentation realized in step b).

6. The method according to claim 1, wherein dung or liquid manure is mixed into the lignocellulose-containing biomass before or during mixing of the lignocellulose-containing biomass in step a) and/or before or during the first anaerobic fermentation and/or the second anaerobic fermentation.

* * * * *